(12) United States Patent
Schröter

(10) Patent No.: US 10,433,777 B2
(45) Date of Patent: Oct. 8, 2019

(54) DETECTION DEVICE FOR VITAL SIGNS

(75) Inventor: Klaus Schröter, Berlin (DE)

(73) Assignee: ASMAG-Holding GmbH, Gruenau im Almtal (AT)

( * ) Notice: Subject to any disclaimer, the term of this patent is extended or adjusted under 35 U.S.C. 154(b) by 480 days.

(21) Appl. No.: 12/812,312

(22) PCT Filed: Jan. 9, 2009

(86) PCT No.: PCT/AT2009/000003
§ 371 (c)(1),
(2), (4) Date: Dec. 22, 2010

(87) PCT Pub. No.: WO2009/086575
PCT Pub. Date: Jul. 16, 2009

(65) Prior Publication Data
US 2011/0087080 A1  Apr. 14, 2011

(30) Foreign Application Priority Data
Jan. 9, 2008  (AT) ........................ 29/2008

(51) Int. Cl.
*A61B 5/01*   (2006.01)
*A61B 5/145*  (2006.01)
(Continued)

(52) U.S. Cl.
CPC .......... *A61B 5/14552* (2013.01); *A61B 5/002* (2013.01); *A61B 5/024* (2013.01);
(Continued)

(58) Field of Classification Search
CPC ............... A61B 5/002; A61B 5/14552; A61B 2560/0219; A61B 2560/0412; A61B 2562/164; A61B 2562/247
(Continued)

(56) References Cited

U.S. PATENT DOCUMENTS

| 5,228,449 A | 7/1993 | Christ et al. |
| 2003/0174049 A1 | 9/2003 | Beigel et al. |

(Continued)

FOREIGN PATENT DOCUMENTS

| DE | 10061299 A1 | 6/2002 |
| DE | 102004048864 A1 | 4/2006 |

(Continued)

OTHER PUBLICATIONS

International Search Report, PCT/AT2009/000003, dated May 11, 2009.

*Primary Examiner* — Gary Jackson
*Assistant Examiner* — Zahed Kabir
(74) *Attorney, Agent, or Firm* — Collard & Roe, P.C.

(57) ABSTRACT

The invention relates to a device (1) for detecting vital signs comprising a sensor (2) and a power supply module (3), which sensor (2) has at least one detection means (5, 6, 7, 8) configured to detect a vital sign from the group comprising oxygen content of the blood, body temperature, skin moisture, conductivity of the skin, pulse, and a first (10) communication module, and the power supply module (3) has a second communication module (20) and a power source (21), and a wireless communication link (4) exists between the first (10) and second communication module (20), and the sensor (2) is provided in the form of an elastically deformable, rebounding thin-film sensor, and the communication link (4) is configured for transmitting power and measured values or measurement data.

12 Claims, 2 Drawing Sheets

Figure 2B:
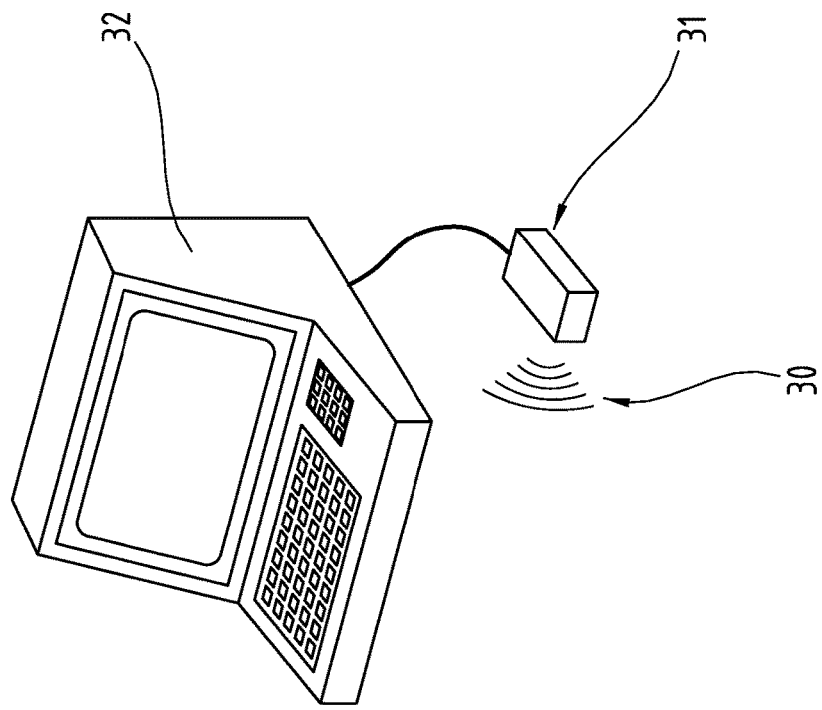

(51) Int. Cl.
*A61B 5/053* (2006.01)
*A61B 5/024* (2006.01)
*A61B 5/1455* (2006.01)
*A61B 5/00* (2006.01)
*A61B 5/0205* (2006.01)

(52) U.S. Cl.
CPC ......... *A61B 5/02055* (2013.01); *A61B 5/0531* (2013.01); *A61B 2560/0219* (2013.01); *A61B 2560/0412* (2013.01); *A61B 2562/028* (2013.01); *A61B 2562/164* (2013.01); *A61B 2562/247* (2013.01)

(58) Field of Classification Search
USPC ................................ 600/300, 301, 323, 324
See application file for complete search history.

(56) References Cited

U.S. PATENT DOCUMENTS

| | | | |
|---|---|---|---|
| 2003/0181817 A1* | 9/2003 | Mori | A61B 5/0002 600/500 |
| 2005/0197540 A1 | 9/2005 | Liedtke | |
| 2005/0228296 A1 | 10/2005 | Banet | |
| 2005/0245793 A1* | 11/2005 | Hilton et al. | 600/300 |
| 2006/0066449 A1 | 3/2006 | Johnson | |
| 2007/0020445 A1* | 1/2007 | Liu | B81C 99/008 428/195.1 |
| 2007/0078318 A1* | 4/2007 | Kling et al. | 600/323 |
| 2007/0093707 A1 | 4/2007 | Noguchi | |
| 2007/0106133 A1 | 5/2007 | Satchwell et al. | |
| 2007/0106172 A1* | 5/2007 | Abreu | 600/549 |
| 2007/0123756 A1 | 5/2007 | Kitajima et al. | |
| 2007/0129613 A1 | 6/2007 | Rochester et al. | |
| 2007/0219440 A1* | 9/2007 | Hannula et al. | 600/323 |
| 2007/0237678 A1 | 10/2007 | Roesicke et al. | |
| 2007/0255330 A1* | 11/2007 | Lee | A61N 1/37288 607/32 |
| 2007/0265677 A1* | 11/2007 | Giftakis et al. | 607/45 |
| 2007/0299330 A1* | 12/2007 | Couronne et al. | 600/368 |
| 2007/0299473 A1* | 12/2007 | Matos | 607/5 |
| 2008/0033271 A1* | 2/2008 | Say et al. | 600/347 |
| 2008/0045806 A1* | 2/2008 | Keppler | 600/300 |
| 2008/0061961 A1* | 3/2008 | John | 340/539.12 |
| 2008/0071328 A1* | 3/2008 | Haubrich | A61B 5/0031 607/60 |
| 2008/0076974 A1 | 3/2008 | Yamazaki et al. | |
| 2008/0129486 A1 | 6/2008 | Jeckelmann et al. | |
| 2008/0139899 A1* | 6/2008 | Student et al. | 600/301 |
| 2008/0167535 A1* | 7/2008 | Stivoric et al. | 600/301 |
| 2009/0105605 A1* | 4/2009 | Abreu | 600/549 |
| 2009/0118595 A1* | 5/2009 | Greiner et al. | 600/301 |
| 2009/0171178 A1* | 7/2009 | He | A61B 5/0031 600/365 |
| 2009/0231125 A1 | 9/2009 | Baldus et al. | |
| 2009/0264714 A1 | 10/2009 | Chou | |
| 2010/0056886 A1 | 3/2010 | Hurtubise et al. | |
| 2010/0168530 A1* | 7/2010 | Chetham et al. | 600/301 |

FOREIGN PATENT DOCUMENTS

| | | |
|---|---|---|
| EP | 1532923 A1 | 5/2005 |
| GB | 2408209 A | 5/2005 |
| JP | H11028196 A | 2/1999 |
| JP | 2001057966 A | 3/2001 |
| JP | 2003144417 A | 5/2003 |
| JP | 2003275183 A | 9/2003 |
| JP | 2007105316 A | 4/2007 |
| JP | 2007117157 A | 5/2007 |
| JP | 2007209428 A | 8/2007 |
| JP | 2007313299 A | 12/2007 |
| WO | 2005048830 A1 | 6/2005 |
| WO | 2006005169 A1 | 1/2006 |
| WO | 2006064397 A2 | 6/2006 |
| WO | 2006114297 A1 | 11/2006 |
| WO | 2007028035 A2 | 3/2007 |
| WO | 2007137498 A1 | 12/2007 |

\* cited by examiner

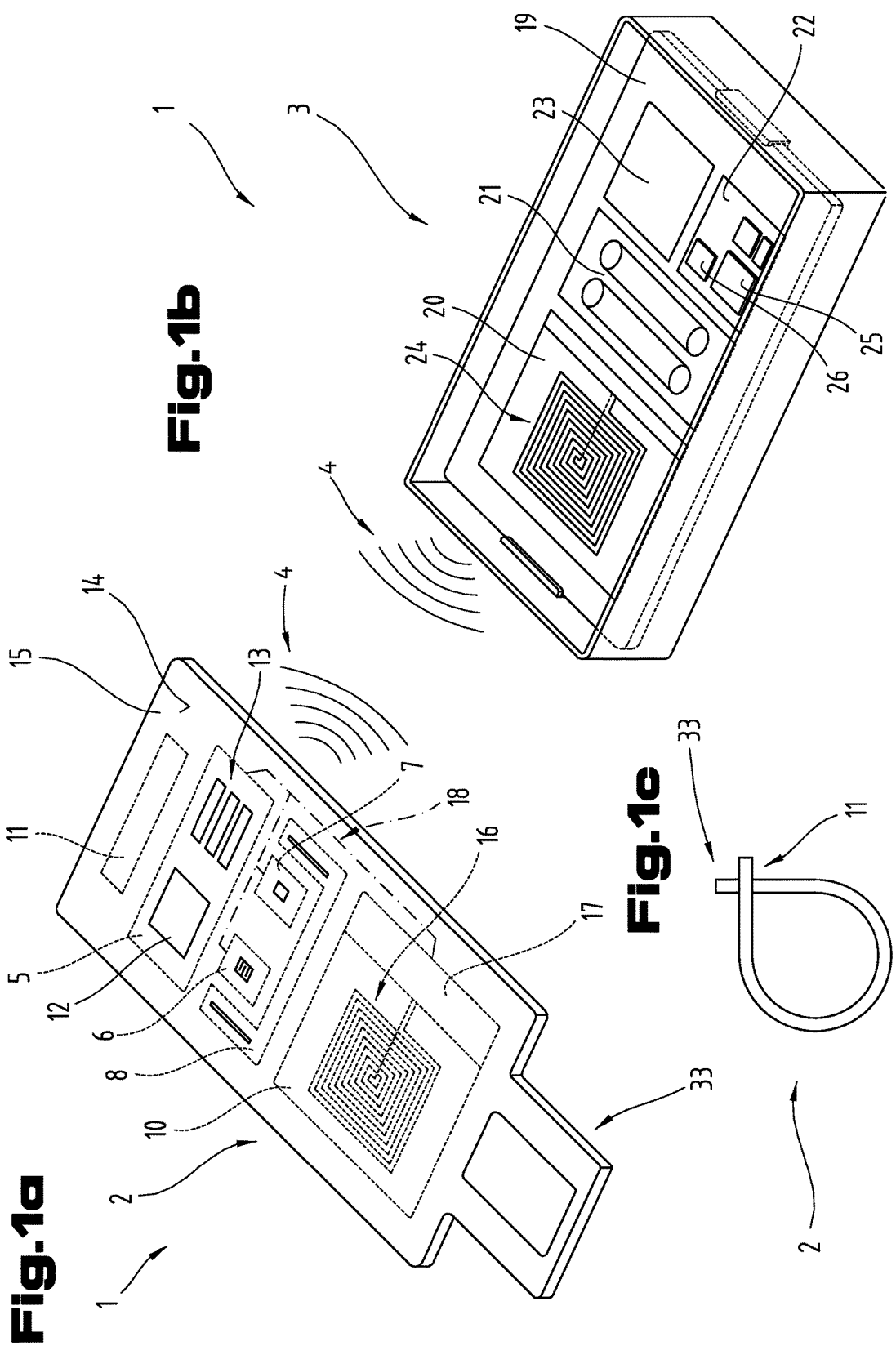

DETECTION DEVICE FOR VITAL SIGNS

CROSS REFERENCE TO RELATED APPLICATIONS

The present application is a national phase entry under 35 U.S.C. § 371 of International Application No. PCT/AT2009/000003, filed Jan. 9, 2009, published in German, which claims the benefit of Austrian Patent Application No. A 29/2008, filed Jan. 9, 2008. The disclosures of said applications are incorporated by reference herein.

The invention relates to a device for detecting vital signs.

In order to provide permanent medical monitoring of a person or to monitor a training program or keep a log, it is necessary to detect vital signs at regular intervals. In order to make the process as pleasant as possible for the person being monitored, it is of particular advantage to design a monitoring device so that it is inconspicuous to the wearer of the device. It is of particular advantage that such a monitoring device should not restrict the freedom of movement of the wearer or should do so to only a negligible degree. It is also of advantage to ensure that operation continues for as long as possible.

Patent specification WO 2006/005169 A1 discloses a device and a method of monitoring vital signs, where the patient wears an evaluating device on the wrist and an optical detection device is held in the hand. The optical detection device is designed in the form of a ring, for example, which is worn around a finger, preferably the thumb.

Patent specification WO 2005/048830 A1 discloses a device for detecting vital signs. To this end, the device is disposed in a housing, and metal contact electrodes are provided on the external face of the housing. In order to detect vital signs, the user must manually apply the device to a point of the body. The detected data is transmitted via a long-range communication means to a contact person in a control center, for example.

The disadvantage of the devices known from the prior art is that a device has to be worn on the wrist and the detection means has to be held in the hand. It is also a disadvantage if the device has to be held or applied against the body by the user in order to take measurements. The known devices are also usually of a not inconsiderable size and thus significantly restrict the user's freedom of movement or allow only a severely limited amount of movement during the measuring operation.

The objective of the invention is to propose an autarchic device by means of which vital signs can be detected continuously over a long period, and a means for detecting the vital signs can be positioned on the wearer's body so that it does not restrict the wearer's freedom of movement or does so to only a negligible degree.

The objective of the invention is achieved due to the fact that the sensor is provided in the form of an elastically deformable and rebounding thin-film sensor and the communication link is programmed to transmit power and measured values or measurement data Opting for a thin-film sensor, the individual active layers are applied to a substrate by vapor deposition and/or printing. The main advantage resides in the fact that these thin layers can be adapted particularly well to the deformations of the sensor. Since the sensor of the detection device proposed by the invention is disposed on body parts and is also subjected to dynamic deformations due to the movement of the body, it is of vital importance to ensure that the sensor is not damaged due to mechanical stress when used for its intended purpose in order to ensure reliable operation.

Likewise with respect to wearer comfort and hence acceptance by the user, it is of advantage if the communication link is able to transmit electrical power and data. Detection means detecting vital signs require electrical power which must be supplied to the sensor, and this usually takes place via a power source. However, the disadvantage of known power sources is that, for reasons relating to capacity, they are of a not inconsiderable volume and weight and therefore restrict wearing comfort when fitted on the sensor so that the user regards the sensor as an annoying part. Due to low capacity, the disadvantage of a small volume power source is that it can be used for a very limited period only. Since the electrical power is transmitted to the sensor via the communication link, the sensor can be made to a significantly more compact and lightweight design without limiting the period during which the detection device proposed by the invention can be used to any major degree.

A particular advantage can be gained if the first communication link is based on the near field of the skin. Opting for this design means that the sensor can be placed at any point of the body without having to worry about wiring. In particular, the advantage of this embodiment is that the sensor can preferably be placed at those body positions where the vital signs to be detected can be detected particularly readily. The sensor can also be positioned so that it is afforded protection or it can also be positioned so that it does not restrict the wearer's freedom of movement. This is of particular advantage when detecting training data because the sensor can be positioned accordingly so that it does not restrict the natural movements of the person training.

It is also of advantage if the range of the first communication link can be set to prevent interference from a second detection device worn by another patient.

In another advantageous embodiment, the first communication link may also be provided in the form of a high frequency connection of short range, for example an HF connection in the license-free ISM range (Industrial, Scientific, and Medical Band) of 868 respectively 915 MHz. Opting for a communication link in this frequency range means that there are numerous communication devices such as transmitter/receiver circuits available, due to their widespread use.

Another advantageous embodiment enables the oxygen content of the blood to be determined by means of pulse oximetry. In order to run the pulse oximetry method, it is necessary to have a detection means comprising a source for electromagnetic radiation and an electromagnetic radiations detector. With this, capillary vessels are illuminated with light of different wavelengths and the respective different absorption rates are correlated with one another. By establishing a ratio and comparing it with reference values, the degree of oxygen saturation can be determined, and this evaluation can then be run in an external evaluation device, for example. In order to take the measurement, light with a wavelength in the range of 660 nm and in the range of 940 nm is used. Ambient light may also be used if necessary.

The radiation source may be any light-emitting semiconductor components but light emitting diodes are used by preference. As the detector, it is preferable to use a photo transistor although all other photo-sensitive electronic components could also be used.

In other embodiments, the detection means may also detect vital signs such as blood pressure or blood sugar content, for example. A major advantage of these embodiments is that these vital signs can also be detected noninvasively, and in particular an optically operated detection system as claimed enables such vital signs to be detected. It would also be conceivable to provide a detection means for detecting breathing frequency.

A particularly practical advantage can be gained if the detection means is made up of organic and/or inorganic semiconductor components. In terms of the preferred application of the sensor, detection means comprising organic semiconductor components offer a particular advantage in that they can be manufactured particularly easily, quickly and inexpensively. With respect to environmental issues and disposal, organic semiconductors offer an additional advantage in that they do not require any processes which involve high energy consumption or high temperature processes and the sensor can be disposed of without risk to the environment. In situations where vital signals have to be detected continuously, the detection means of the sensor can become dirty, thus impairing or limiting the functionality of the sensor or even rendering it unusable. Given the advantages outlined above, it is now possible to design a disposable sensor, so that it is no longer necessary to clean a dirty sensor and instead, it can be replaced immediately by a new sensor.

Organic semiconductor components and in particular organic light-emitting diodes and organic photo-transistors have long been known from the prior art and therefore require no further description here.

In the case of another advantageous embodiment, the detection means may also be provided in the form of inorganic semiconductor components or a combination of organic and inorganic semiconductor components.

Based on another embodiment, the sensor is provided in the form of a flat support layer on which the detection means is disposed. The advantage of an elastically deformable and rebounding flat support layer is that it can be adapted particularly well to the surface structure on which the sensor is disposed. The support layer may be made from PEN or PET, for example.

In the case of another advantageous embodiment, the flat support layer may be of an electrically insulating type, in which case the detection means can be applied to the support layer without an additional electrically insulating protective layer. Another advantage is the fact that the support layer is preferably supplied as a film material on a roll, offering a particularly rational method of producing the sensor, especially using continuous processing.

Based on another advantageous embodiment, the optically acting detection means may also be disposed on the flat face of the support layer facing away from the body part. If the support layer is transparent or semi-transparent at least in the spectral range of the radiation source or the radiation detector, there is no need for the detection means to be placed on the body surface where it is exposed to a greater risk of becoming dirty.

A very decisive advantage can be obtained if the detection means is printed on a flat face of the support layer. Detection means produced by printing processes, for example inkjet printing, screen printing or stamping are particularly inexpensive. The particular advantage of printing processes is that they can be adapted to changing requirements very rapidly and flexibly, so that even small numbers of items can be produced economically. It is also possible to produce complex structures of the type needed for semiconductor components much more easily and quickly with printing processes. In particular, the detection means can be printed onto prefabricated components.

Based on another advantageous embodiment, the detection means is made up of organic semiconductor components. Organic semiconductor materials are particularly practical for use in printing processes and enable layouts to be obtained which can not be obtained using inorganic semiconductor materials, or can be so only with great difficulty. For example, during a first printing operation, a portion can be left free and another material printed into it in a second printing operation. If using inorganic materials, complex lithography and etching processes would have to be used.

In terms of user friendliness, it is of advantage to opt for an embodiment in which the sensor can simply be fitted and removed. In a manner generally known, a cuff is designed so that it is at least of a length in its longitudinal extension which is necessary to enclose the requisite circumference. The cuff may be a closed cylindrical cuff, in which case the fine adjustment to the circumference is preferably obtained using elastic portions. However, the cuff may also be a developed cylinder, in which case the cuff is designed to suit the circumference to be enclosed and is positioned on it by means of a retaining means.

Also of advantage is another embodiment in which the cuff has a closure element designed to emit a trigger signal. It is then only necessary to measure the vital signals when the sensor is applied to a body part. If the closure element is designed to emit a trigger signal, this signal can be used to activate the detection device, after which vital signals are detected periodically. This embodiment advantageously prevents incorrect measurements. For example, the sensor can become detached from the body unnoticed, after which vital signals will no longer be detected and an alarm could be used to indicate such a state, for example. As defined in the claim, however, a trigger signal is generated if the sensor becomes detached from the body and an alarm alert due to the absence of vital signs is suppressed. The trigger signal triggered if the sensor inadvertently becomes detached from the body could also be used to alert the wearer to this fact. The claimed embodiment therefore offers a significant increase in operating safety and comfort for the user.

As proposed by the invention, power is transmitted from the power supply module to the sensor via a wireless communication link. If a storage is provided in the first communication module for electrical power, detection means which require higher power consumption can be fitted on the sensor. As proposed by the invention, vital signs are not detected continuously but in a pre-selectable time pattern, for example every minute. Since only a limited amount of power can be transmitted via the wireless communication link, the claimed embodiment offers an advantage in that the power storage can be charged during the pauses between measurements. During measurements, the detection means are supplied with electrical power by the power storage. The measuring cycles are selected so that the time between measuring operations is enough for the power storage to be charged with enough power to enable the next measuring operation to be run.

The power storage is provided in the form of a capacitive storage or an electrochemical storage element. A particularly advantageous embodiment is one in which the power storage is provided in the form of a thin-film element or a polymer accumulator because a power storage of this type can be produced by printing.

Based on another advantageous embodiment, the first and second communication module has a device for transmitting and/or receiving electromagnetic radiation. The transmitter and/or receiver device is configured so as to transfer electrical power, control signals and detected measurement values applied to the first and second communication module to an electromagnetic field so that the wireless communication link is established between the first and second communication module.

Based on yet another embodiment, the communication link is established on the basis of the near field of the skin. In this case, the transmitter and/or receiver device of the first and second communication modules must be configured so that the electromagnetic radiation can be coupled with the transport medium, namely the skin. Since electrical power has to be transmitted via the communication link in order to supply the sensor in addition to measured values and control signals, a frequency of 100 kHz for the electromagnetic alternating signal has proved to be of particular advantage.

The transmitter and/or receiver device may be provided in the form of an antenna, for example, or a printed strip conductor antenna. A transmitter and/or receiver device based on this design can advantageously be fitted very easily on the sensor or integrated in it.

Also of advantage is an embodiment in which the power source is provided in the form of an element from the group comprising a chemical element, an inorganic or organic solar cell. Since the power supply module is disposed at a distance from the sensor, in other words the wearer's freedom of movement is barely restricted at all, a device with a higher capacity may also be used as the power source. In particular, widely available, inexpensive and very high capacity chemical elements may be used. To permit autarchic power operation of the detection device proposed by the invention, it is also of advantage if the power source is a solar cell, in particular an organic solar cell. The particular advantage of organic solar cells is that they are particularly inexpensive and can be manufactured economically, especially if manufactured by printing processes.

A decisive advantage of the claimed embodiment is that the supply of electrical power to the sensor takes place via the power supply module. Since it is not necessary to provide a power source on the sensor, it can be made to a particularly compact design, which is of advantage in terms of gaining high acceptance on the part of the user because a compact sensor does not or only slightly restricts freedom of movement and is therefore not perceived as annoying.

In order to process the detected measurement values, it is of advantage to provide the power supply module with an evaluation device. The vital signals detected by the detection means are therefore available as so-called raw data, which must be processed in readiness for determining the data. This processing task can then advantageously be dealt with by the evaluation device of the power supply module. In the example of detecting the oxygen content of the blood, brightness values are detected, for example. Based on the known method of pulse oximetry, the individual brightness values for different spectral components are correlated with one another and this task can be handled by the evaluation device, which means that the evaluation device will be capable of providing values proportional to the oxygen content. However, the evaluation device may also be configured so that it aggregates the periodically detected vital signs in order to enable a long-term trend to be determined. In another advantageous embodiment, the evaluation device may also have an alarm device, for example, which alerts the wearer if a vital sign rises above or drops below a threshold value.

In order to run the routine of processing the measurement values, it is of advantage if the evaluation device has a control unit and a memory. Rules can be stored in the memory, which can be loaded by the control unit and run in order to run the routine of processing the detected vital signs. The control unit may also be provided in the form of a micro-computer and the memory may be a volatile or non-volatile memory module. The memory may also be configured so that it temporarily stores detected and processed vital signs until the next data synchronization.

The detection device proposed by the invention may be operated independently, in which case monitoring, evaluation and optionally alerting the wearer to alarms can be handled on an autarchic basis without the intervention or involvement of a data evaluation device. The detection device proposed by the invention may also be configured so that it allows personal vital data to be evaluated by an analysis device. In this case, it is of particular advantage if the power supply module has a third communication module. This third communication module is preferably configured to establish a wireless communication link, although it would also be conceivable to connect an analysis device by cable. In any event, the third communication module is configured to convert the detected and optionally processed measurement values of the vital signals into a format that permits transmission.

In accordance with another advantageous embodiment, the third communication module is configured to establish a data link with a data distant end of a data analysis unit. The data link may be provided in the form of a wireless communication link operating in the local range, for example RFID, Bluetooth, IrDA. The third communication module and the data distant end thus have a transmitter and/or receiver device. However, the data link may also be a hard-wired communication link, for example USB.

Another advantageous embodiment can be obtained if the third communication module is a memory module, as claimed. In order to transmit the detected vital signals to the data analysis unit, the user, but more especially the power supply module, must be in the vicinity of the data distant end of the data analysis unit in order to establish the data link. If the third communication module has a memory module, the detected vital signals can be temporarily stored for a definable period by the capacity of the memory module and will not be transmitted to the data analysis unit until later when a data link is established. This is of particular advantage if vital signs have to be detected for long periods because the wearer of the detection device proposed by the invention can not be expected to establish the data link with the data analysis unit in order to synchronize the detected vital signs too often. Particularly preferred is an embodiment in which the memory module holds the stored contents without a supply of electrical power.

The advantage of wearing the power supply module in or on the user's clothing is that the power supply module is positioned so that it is as inconspicuous as possible but does not restrict the user's freedom of movement. However, the power supply module may optionally also be disposed on the body surface, for example by attaching it to an elastic strap. It is of particular advantage to dispose the power supply module on the body surface if the communication link is established by the near field of the skin because it is possible to obtain a particularly good coupling and uncoupling of the electromagnetic fields on the skin surface. However, in order to establish a communication link by means of the near field of the skin, direct skin contact is not necessary and in particular, it is sufficient for the power supply module, in particular the second communication module, to be placed within a close range of several cm distance from the skin surface.

With a view to obtaining autarchic operation of the detection device for the longest possible time and in particular with a view to obtaining as compact as possible a sensor, it is very much of advantage if the power supply module is configured to activate the sensor. Vital signs do not have to be detected continuously and detection on a periodic basis will suffice, for example every minute. To enable a sensor design that is compact and consumes as little energy as possible, it is therefore of advantage is this time control is not run on the sensor, which would require a permanent power supply, and instead, the sensor is activated by an external time transmitter. The power supply module may therefore incorporate a time transmitter, which activates the sensor periodically via the communication link. The time transmitter is preferably disposed in the evaluation device or comprises it. Activation may operate in such a way that a signal with a special frequency is emitted by the second communication module, to which an activation device in the first communication module is selective and thus activates the detection means. Once the vital signs have been detected, they are transmitted via the communication link to the power supply module and the sensor is deactivated again. The power-consuming operation of detecting the vital signs is therefore active for only a short period of the entire operating time, resulting in a significant extension of the usage time due to the lower power consumption, thereby also enabling more compact modules to be used.

The invention will be described in more detail below on the basis of examples of embodiments illustrated in the appended drawings.

Figure 2A:
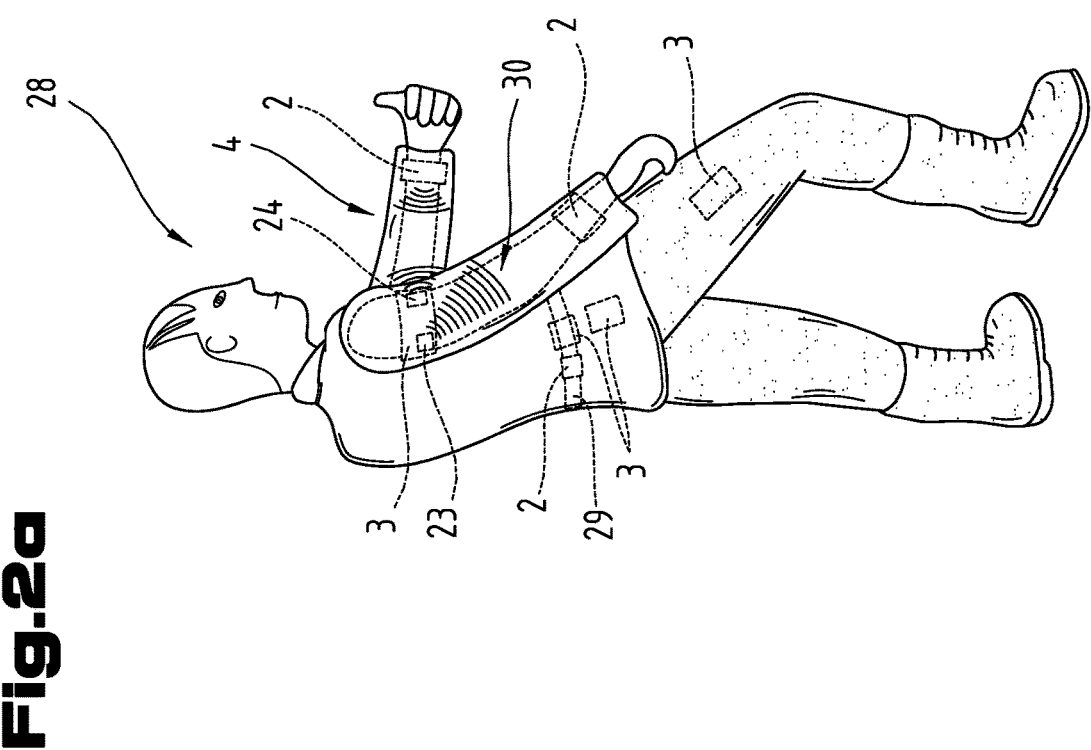

These show schematic diagrams as follows:

FIG. 1*a* shows an embodiment of the flexible sensor of the detection device proposed by the invention;

FIG.. 1*b* shows an embodiment of a power supply module according to the invention;

FIG.. 1*c* shows the embodiment of the flexible sensor from FIG. 1*a* in a looped-around and closed position;

FIG. 2*a* shows a person wearing several embodiments of the detection device; and FIG. 2*b* shows a data analysis unit which can synchronize with the detection device to obtain the detected vital signs.

Firstly, it should be pointed out that the same parts described in the different embodiments are denoted by the same reference numbers and the same component names and the disclosures made throughout the description can be transposed in terms of meaning to same parts bearing the same reference numbers or same component names. Furthermore, the positions chosen for the purposes of the description, such as top, bottom, side, etc., relate to the drawing specifically being described and can be transposed in terms of meaning to a new position when another position is being described. Individual features or combinations of features from the different embodiments illustrated and described may be construed as independent inventive solutions or solutions proposed by the invention in their own right.

All the figures relating to ranges of values in the description should be construed as meaning that they include any and all part-ranges, in which case, for example, the range of 1 to 10 should be understood as including all part-ranges starting from the lower limit of 1 to the upper limit of 10, i.e. all part-ranges starting with a lower limit of 1 or more and ending with an upper limit of 10 or less, e.g. 1 to 1.7, or 3.2 to 8.1 or 5.5 to 10.

Figs. 1*a*, 1*b*, and 1*c* illustrate the detection device 1 proposed by the invention, comprising a sensor 2 and power supply module 3, and a short-range wireless communication link 4 exists between these two.

The sensor 2 has a means 5 for detecting the oxygen content of the blood, a means 6 for detecting body temperature, a means 7 for detecting skin moisture and a means 8 for detecting the conductivity of the skin, for example. The sensor 2 further comprises a first communication module 10 and optionally a closure element 11 configured to act with the closure element 33 to secure the sensor 2 around an object. FIG. 1*c* shows the sensor 2 in a looped-around and closed position with the closure element 33 engaging through the closure element 11.

The means 5 for detecting the oxygen content of the blood is provided in the form of an electromagnetic radiation detector 12 and at least one source of electromagnetic radiation 13. The detection means 5 detects the oxygen content of the blood using the method of pulse oximetry. To this end, electromagnetic radiation with a first wavelength in the optically visible range, for example in the range of 660 nm, is emitted by a radiation source 13, and electromagnetic radiation in another wavelength range, for example in the range of 940 nm, is emitted by a second radiation source. Due to the hemoglobin saturated with oxygen, the radiation is weakened to a different degree in each case. The radiation detector 12 is photosensitive in the entire wavelength range of the light emitted by the radiation source 13 and generates an output signal or an electric voltage proportional to the intensity of the incident electromagnetic radiation. The detector may also vary its resistance or some other electrical variable depending on the intensity of the incident electromagnetic radiation. The radiation source 13 is preferably provided in the form of a light-emitting diode (LED) and the radiation detector 12 is preferably provided as a quantum detector, for example a photo-detector or photo-diode. In the case of one particularly preferred embodiment, the radiation source 13 and the radiation detector 12 are organic semiconductors or organic semiconductor components, which are printed onto a flat face 14 of the support layer 15. The printing methods used to produce organic semiconductors are, for example, inkjet printing, screen printing, stamp printing. The advantages of using a printing method are that the components and structures to be created can be produced particularly easily, inexpensively and to individual designs. Printing methods do not require any particularly energy-intensive production steps, for example evaporation under a high vacuum, and printing methods also enable layered structures of semiconductor materials to be produced, which would not be possible if using inorganic semiconductors, or would be so but only at great expense. In particular, the components to be produced can also be printed onto semi-finished parts at a later stage.

The means for detecting body temperature is provided in the form of an electronic component, for example, and the value of at least one electrical variable is dependent on temperature. For example, heat or cold conductors may be used, but also electronic semiconductor components for measuring temperature because the current/voltage curve of a semiconductor junction is dependent on temperature.

The means for detecting skin moisture may be designed so that an infrared radiation source, for example an IR-LED, emits light which hits the skin and is reflected by the upper skin layers. The higher the water content of the skin layer, the greater the amount of infrared light reflected. By opting for an appropriate design and disposition of the radiation source 13 and detector 12 of the means 5 for detecting the oxygen content of the blood, skin moisture can also be detected by the detection means.

In order to determine the conductivity of the skin, a harmless electrical voltage is applied to two electrodes of the detection means 8, for example, and the electrical current flowing through the skin is measured. In another advantageous embodiment, the conductivity of the skin can also be determined by determining the water content of the skin using the detection means 7.

The first communication module 10 is also disposed on the sensor 2. The transmitter and/or receiver device 16 is preferably provided in the form of an antenna for irradiating and receiving electromagnetic radiation in the free ISM range of 868 respectively 915 MHz. A power storage optionally provided in the first communication module may be provided in the form of a double-layer capacitor. It has a very high power density and a very low self-discharge rate. The communication module 10 or the power storage 17 is configured to supply the detection means 5, 6, 7, 8 with electrical power. The individual detection means are therefore connected to the communication module 10 or power storage 17 via an electrical connecting wire 18.

The sensor 2 is preferably designed as a cuff which is placed around a body part, and in order to secure the cuff on the body part, the cuff is closed by means of a closure element 11. When the cuff is closed by the closure element 11, a trigger signal is generated and emitted and is transmitted via the communication link 4 to the power supply module 3. From this trigger signal, the power supply module knows that the sensor has been fitted and in particular detects when the sensor is removed. The advantage of this embodiment is that vital signs can not be detected unless the sensor is fitted. In particular, this also prevents erroneous failure alarms in the absence or cessation of vital signs if the cuff is removed.

The support layer 15 of the sensor is preferably provided in the form of a flexible, flat material. The detection means 5, 6, 7 and 8 may therefore be disposed on the flat face 14 of the support layer 15 so that they are in direct contact with the skin surface when the cuff is fitted. However, it would also be possible to cover the detection means with a protective layer but in this case, there must always be respective portions in which the active variable can be input and output to and from the detection means. In the case of another advantageous embodiment, the support layer 15 may be provided in the form of a transparent or semi-transparent material, for example, such as PET or PANI. The advantage of this design is that optically operated detection means can also be placed on the flat face of the support layer facing away from the skin surface without impairing the optical active signals. It is particularly preferable to opt for a design in which the detection means 5, 6, 7 and 8 as well as the first communication module 10 are printed onto the flat face 14 of the support layer 15. This is of particular advantage if the detection means are provided in the form of electronic components made from organic semiconductor material.

The power supply module is provided in the form of a flat support layer 19, for example, on which the second communication module 20, power source 21, an evaluation device 22 and a third communication module 23 are disposed. The second communication module 20 has a transmitter and/or receiver device 24 for transmitting and receiving an electromagnetic wave constituting the communication link 4. The power supply module 3 is configured to supply the sensor 2 with electrical power via the communication link 4 and to receive from it the measurement values of the detected vital signs. Control data may also be transmitted if necessary, for example the activation signal at the sensor and/or the trigger signal of the closure means.

The power source 21 is preferably provided in the form of electrochemical power storage means such as batteries and accumulators. In the case of one advantageous embodiment, the power source may also be provided in the form of a solar cell, and more preferably an organic solar cell. A particularly preferred design is one where the power storage is produced by a thin-film process, for example a printable polymer accumulator.

It is of particular advantage if the power consumption of the sensor, in particular the detection means, is very low because during measurement pauses, the power storage has to be supplied with electrical power again by a power transmission via the skin. The smaller the amount of electrical power which has to be transmitted, the lower the level of electromagnetic fields to which the human body is exposed. In this connection, the International Radiation Protection Association (IRPA) has set threshold values for field intensities which may be allowed to act on the human body. In particular, a threshold value of 80 mW/kg was set for the Specific Absorption Rate (SAR) a threshold value of 250 mA/m$^2$ (rms) for the current density (S).

In a particularly advantageous manner, the device proposed by the invention enables the sensor to be reliably supplied with electrical power without the human organism being exposed to excessive radiation, whilst nevertheless providing a sufficiently high detection rate of vital signs.

In order to evaluate and process the detected vital signs, the power supply module may also have an evaluation device 22 comprising at least a control unit 25 and a memory 26. For example, in order to determine the oxygen content of the blood, it is necessary to compare and evaluate two measured values detected in different spectral ranges. To this end, operating instructions can be stored in the memory 26, which are loaded by the control unit 25 and run, as a result of which a measurement figure is determined representing the oxygen content of the blood. It would naturally also be possible to store other operating instructions. With a view to enabling monitoring over long periods, the measurement figures determined in this manner can also be stored in the memory 26, the advantage of which is that the user only has to transmit the detected data to the data analysis unit at infrequent intervals.

In order to transmit the detected vital signs to the data analysis unit, the power supply module 3 has a third communication module 23 which is configured to establish a data link to a data distant end of a data analysis unit. This data link is preferably operated by a wireless, short-range connection, for example Bluetooth, RFID, IrDA. The third communication module 23 may also have a memory 27, which is of particular advantage if no evaluation device 22 is provided, for example, or the storage capacity of the evaluation device is not sufficient to store the detected vital signs temporarily between the individual synchronization operations with the data analysis unit. It is particularly preferable if the memories 26, 27 are provided in the form of non-volatile memory modules because the detected vital signs will be saved even if the power source 21 fails.

FIGS. 2a and 2b illustrate a synchronization operation of the detected vital signs with a data analysis unit. The detection device proposed by the invention is worn by the person 28, and the sensor 2 can be worn on the lower arm, in particular in the region of the wrist, or also in the region of the upper body as shown in FIG. 2a. However, the sensor 2 may specifically be disposed in all body positions where the detection of vital signs can advantageously be readily and reliably detected. The sensor 2 may therefore be designed as a cuff which is closed and hence positioned by a closure element when fitted on the body part. However, on a body part where the sensor based on a cuff design is awkward or restricts the wearer's freedom of movement to too great a degree, the sensor may also be positioned on a body part by means of a retaining device 29.

The power supply module 3 may advantageously be positioned anywhere where it does not restrict the freedom of movement of the wearer 28 or does so to only a negligible degree. Since the communication link 4 is preferably established by the near field of the skin, it is merely necessary to ensure that the power supply module 3 is positioned so that the transmitter and/or receiver device 24 is able to secure a sufficient coupling between the irradiated electromagnetic wave and the skin surface.

The data link 30 to the data distant end 31 of the data analysis unit 32 shown in FIG. 2b is established via the third communication module 23. The data analysis unit may be provided in the form of a commonly available computer system. Such a computer system is programmed to run a software program in order to evaluate the detected vital signs transmitted across the data link 31.

The data link 30 may be configured so that synchronization of the detected vital signs is started automatically, as soon as the user 28 is positioned in the vicinity of the data distant end 31. In particular, however, the data link 30 is configured so that only an authorized power supply module 3, in particular an authorized third communication module 23, can establish a data link to the data distant end 31. This prevents unauthorized or fraudulent recording of personal vital signs by unauthorized third parties.

The embodiments illustrated as examples represent possible variants of the device for detecting vital signs, and it should be pointed out at this stage that the invention is not specifically limited to the variants specifically illustrated, and instead the individual variants may be used in different combinations with one another and these possible variations lie within the reach of the person skilled in this technical field given the disclosed technical teaching. Accordingly, all conceivable variants which can be obtained by combining individual details of the variants described and illustrated are possible and fall within the scope of the invention.

For the sake of good order, finally, it should be pointed out that, in order to provide a clearer understanding of the structure of the device for detecting vital signs, it and its constituent parts are illustrated to a certain extent out of scale and/or on an enlarged scale and/or on a reduced scale.

The objective underlying the independent inventive solutions may be found in the description.

Above all, the individual embodiments of the subject matter illustrated in Figs. FIGS. 1 and 2 constitute independent solutions proposed by the invention in their own right. The objectives and associated solutions proposed by the invention may be found in the detailed descriptions of these drawings.

LIST OF REFERENCE NUMBERS

1 Detection device
2 Sensor
3 Power supply module
4 Communication link
5 Means for detecting the oxygen content of the blood
6 Means for detecting body temperature
7 Means for detecting skin moisture
8 Means for detecting the conductivity of the skin
10 First communication module
11 Closure element
12 Electromagnetic radiation detector
13 Source of electromagnetic radiation
14 Flat face
15 Support layer
16 Transmitter and/or receiver device
17 Power storage
18 Electrical connecting wire
19 Support layer
20 Second communication module
21 Power source
22 Evaluation device
23 Third communication module
24 Transmitter and/or receiver device
25 Control unit
26 Memory
27 Memory
28 User, person, wearer
29 Retaining device
30 Data link
31 Data distant end
32 Data analysis unit

The invention claimed is:

1. A device for detecting vital signs, the device comprising:
a flexible sensor and a power supply module, the flexible sensor being configured as a cuff and having at least one detector designed to detect a vital sign selected from the group consisting of oxygen content of the blood, body temperature, skin moisture, conductivity of the skin, and pulse;
wherein the at least one detector is provided in the form of flexible organic semiconductor material;
wherein the flexible sensor further comprises a first communication module comprising an antenna for transmitting and/or receiving electromagnetic radiation;
wherein the power supply module comprises a second communication module and a power source, the second communication module comprising a transmitter and/or receiver device for electromagnetic radiation;
wherein the power supply module is configured to be disposed in or on clothing of or on a body surface of a user;
wherein a first wireless communication link exists between the first and second communication modules, which first wireless communication link is provided in the form of the near field of the skin and is adapted to transfer measured values or measurement data from the antenna of the first communication module of the flexible sensor to the transmitter and/or receiver of the second communication module of the power supply;
wherein the first wireless communication link provided in the form of the near field of the skin is further adapted to transfer electrical power from the transmitter and/or receiver of the second communication module of the power supply module to the antenna of the first communication module of the flexible sensor,
wherein the flexible sensor is provided in the form of an elastically deformable and rebounding thin-film flexible sensor;
wherein the cuff has a closure element designed to emit a trigger signal as a control signal via the first wireless communication link from the first communication module of the sensor to the second communication module of the power supply module independent of power transmitted to the sensor;
wherein the power supply module is configured to activate the at least one detector of the flexible sensor; and wherein the detector is configured to detect vital signs periodically.

2. The detection device according to claim 1, wherein the at least one detector is designed to detect the oxygen content of the blood and is provided in the form of at least one source of electromagnetic radiation and an electromagnetic radiation detector.

3. The detection device according to claim 1, wherein the flexible sensor is provided in the form of a flat support layer on which the at least one detector is disposed.

4. The detection device according to claim 3, wherein the support layer is of a transparent or semi-transparent design.

5. The detection device according to claim 3, wherein the at least one detector is printed onto a flat face of the support layer.

6. The detection device according to claim 1, wherein the first communication module has a storage for electrical power.

7. The detection device according to claim 1, wherein the power source is provided in the form of an element selected from the group consisting of chemical elements, an inorganic solar cell, and an organic solar cell.

8. The detection device according to claim 1, wherein the power supply module has an evaluation device.

9. The detection device according to claim 8, wherein the evaluation device comprises a control unit and a memory.

10. The detection device according to claim 1, wherein the power supply module has a third communication module.

11. The detection device according to claim 10, wherein the third communication module is configured to establish a data link to a data distant end of a data analysis unit.

12. The detection device according to claim 10, wherein the third communication module has a memory module.

* * * * *